United States Patent [19]

Vletter

[11] Patent Number: Plant 7,218

[45] Date of Patent: Apr. 10, 1990

[54] *ERYNGIUM PLANUM* PLANT NAMED FLUELA

[75] Inventor: Floris Vletter, Rijnsburg, Netherlands

[73] Assignee: Gebr, Vletter & J.A. den Haan, Netherlands

[21] Appl. No.: 260,694

[22] Filed: Oct. 21, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A distinct cultivar of *Eryngium planum* named Fluela characterized by its relatively large and tall growth, rosette form, large peduncles having secondary and tertiary branches, and ellipsoid shaped, violet blue flowers.

3 Drawing Sheets

The present invention comprises a new and distinct cultivar of *Eryngium planum,* commonly called sea holly, known by the cultivar name Fluela.

Fluela originated from a hybridization made by the inventor Floris Vletter in a controlled breeding program in Rijnsburg, the Netherlands covering the years 1980–1982. The female, or seed, parent of Fluela was Ditochterum. The male, or pollen, parent was Seedling PZ-1.2. Fluela was discovered and selected as one flowering plant within the progeny of the stated parentage by the inventor on June 28, 1982 in a controlled environment in Rijnsburg, the Netherlands.

The first act of asexual reproduction of Fluela was accomplished when root cuttings were taken from the initial selection on Aug. 14, 1982 in a controlled environment in Rijnsburg, the Netherlands by a technician working under formulations established and supervised by the inventor. Horticultural examination of selected units, initiated on Sept. 11, 1986, has demonstrated that the combination of characteristics as herein disclosed for Fluela are firmlyfixed and are retained through successive generations of asexual reproduction.

Fluela has not been observed under all possible environmental conditions. The phenotype may vary considerably with variations in environment such as temperature, light intensity and day length. The following observations, measurements and comparisons describe plants grown in Wageningen, the Netherlands under outside conditions which approximate those generally used in commercial practice. Color references are made to The Royal Horticultural Society Colour Chart.

The accompanying photographic drawings show a typical specimen plant of the new cultivar, with colors being as true as possible for color illustrations of this type. Photographic Drawing 1 is a perspective view of the variety in blossom. Photographic Drawing 2 is a closeup perspective view of flowering branches of the variety, showing the peduncle andhead. Photographic Drawing 3 illustrates the foliar rosette form of leaves of the variety.

The following traits have been repeatedly observed and are determined to be basic characteristics of Fluela, which in combination distinguish this *Eryngium planum* as a new and distinct cultivar:

1. Plant is relatively large and tall, with a dense rosette form.

2. Large peduncles, 30 cm. and larger, having secondary and tertiary branches.

3. Medium size, ellipsoid shaped flowers, violet blue in color.

Plant:

*Form.*—Relatively large.

*Size.*—About 90 cm tall when mature.

*Growth habit.*—Rosette is dense and plant has large peduncles.

*Blooming habit.*—Branching flower heads.

Leaf:

*Size.*—Rosette leaves about 14 cm long with petioles of about 16 cm.

*Color.*—Dark green and slightly glossy.

*Quantity.*—Approximately 25.

*Shape.*—Leaf-blade almost elliptical, crenate, leaf margin with short prickles.

Peduncle:

*Size.*—From 30 cm upwards, branching out somewhat wider and then with secondary and tertiary branches.

*Color.*—The main stem silvery-grey with a blue tinge increasing to the top; lateral branches rather intense blue-purple, about R.H.S. 86B-C.

*Stem leaves.*—Stem leaves sessile, leaf blades at the base of the peduncle similar to those of the rosette leaves, ovate upwards along thepeduncle and at the top of the peduncle palmately parted and sharply pricked.

Flowers:

*Size.*—Medium sized, the actual flower size being about 1.7 centimeters in height and a width of 1.5 centimeters.

*Form.*—Ellipsoid, involucral bract, narrow and long and approximately 86B-C on its upper surface (with greyish tinge), underside dark greyish green.

*Color.*—Mature: upper surface, petals of heads are approximately 86 A-B; under surface, greyish green. Immature: upper and lower surfaces light green.

Propagation: The new cultivar is reproduced through successive breeding generations by root cuttings.

I claim:

1. A new and distinct cultivar of *Eryngium planum* named Fluela, as illustrated and described.

* * * * *

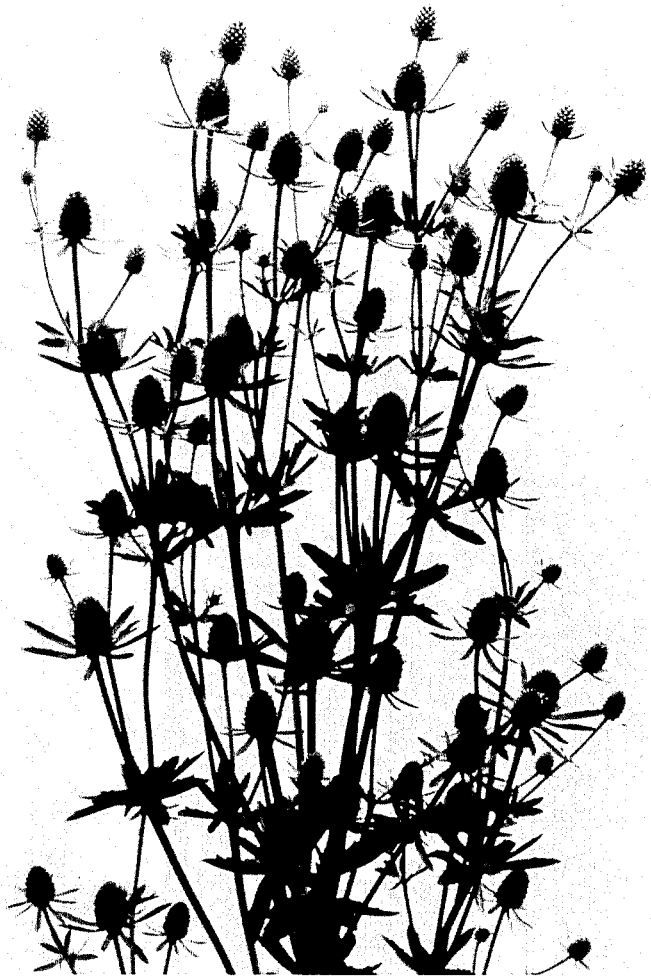

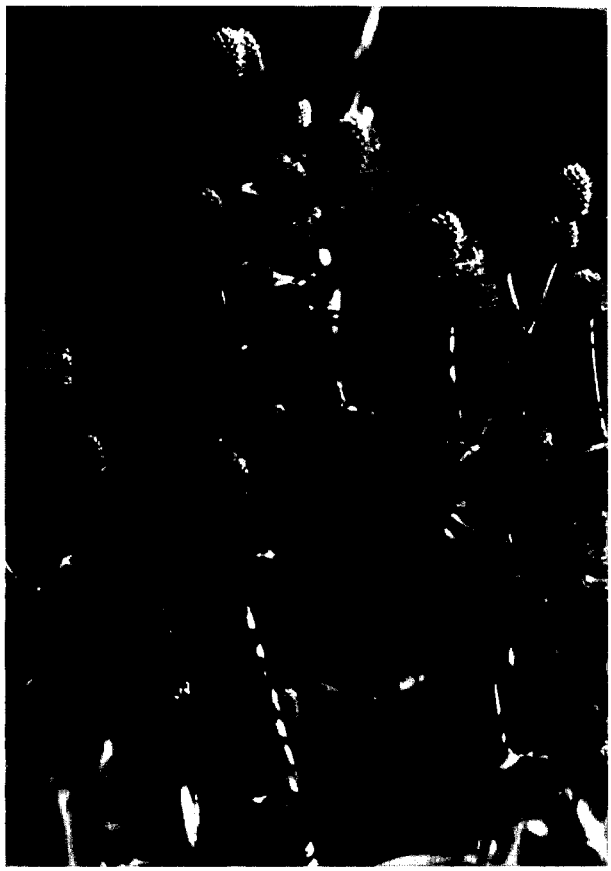

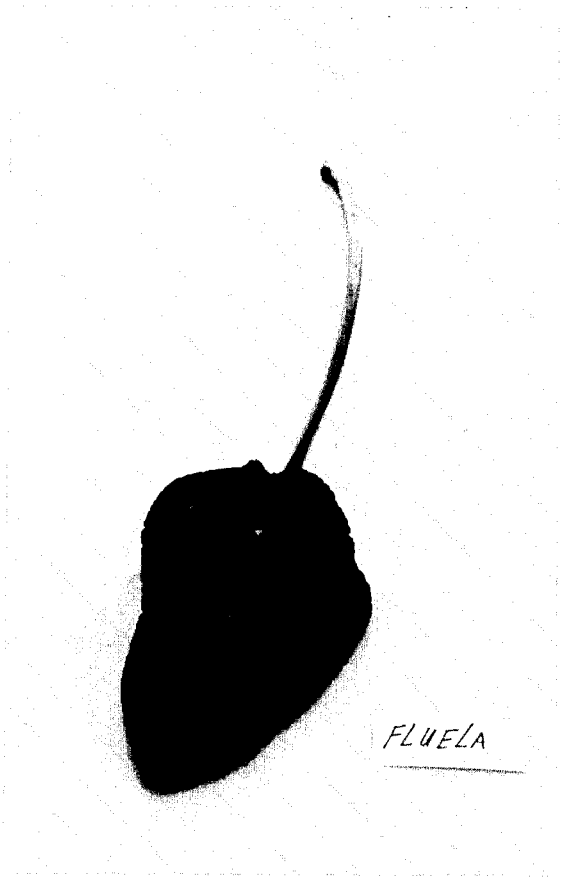
FLUELA